US011130725B2

(12) United States Patent
Brammer et al.

(10) Patent No.: US 11,130,725 B2
(45) Date of Patent: Sep. 28, 2021

(54) METHODS FOR SLOWING DEACTIVATION OF A CATALYST AND/OR SLOWING TETRAPHOSPHINE LIGAND USAGE IN HYDROFORMYLATION PROCESSES

(71) Applicant: Dow Technology Investments LLC, Midland, MI (US)

(72) Inventors: Michael A. Brammer, Freeport, TX (US); Michael C. Becker, Hewitt, TX (US); William N. Felsted, II, Lake Jackson, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 17/040,287

(22) PCT Filed: May 3, 2019

(86) PCT No.: PCT/US2019/030571
§ 371 (c)(1),
(2) Date: Sep. 22, 2020

(87) PCT Pub. No.: WO2019/231610
PCT Pub. Date: Dec. 5, 2019

(65) Prior Publication Data
US 2021/0114961 A1    Apr. 22, 2021

Related U.S. Application Data

(60) Provisional application No. 62/677,858, filed on May 30, 2018.

(51) Int. Cl.
*C07C 45/50* (2006.01)
*B01J 31/00* (2006.01)
*B01J 31/24* (2006.01)

(52) U.S. Cl.
CPC ......... *C07C 45/505* (2013.01); *B01J 31/2409* (2013.01); *B01J 2231/321* (2013.01); *B01J 2531/004* (2013.01); *B01J 2531/822* (2013.01)

(58) Field of Classification Search
CPC .... C07C 45/50; C07C 45/505; B01J 31/2409; B01J 2231/321; B01J 2531/0004; B01J 2531/822
See application file for complete search history.

(56) References Cited

U.S. PATENT DOCUMENTS

| | | |
|---|---|---|
| 3,527,809 A | 9/1970 | Pruett et al. |
| 4,169,861 A | 10/1979 | Hughes |
| 4,215,077 A | 7/1980 | Matsumoto et al. |
| 4,260,828 A | 4/1981 | Morrell et al. |
| 4,283,562 A | 8/1981 | Billig et al. |
| 4,400,548 A | 8/1983 | Abatjoglou et al. |
| 5,110,990 A | 5/1992 | Blessing et al. |
| 5,237,106 A | 8/1993 | Babin et al. |
| 5,741,945 A | 4/1998 | Bryant et al. |
| 5,767,321 A | 6/1998 | Billig et al. |
| 6,153,800 A | 11/2000 | Gelling et al. |
| 7,531,698 B2 | 5/2009 | Zhang et al. |
| 7,709,659 B2 | 5/2010 | Zhang et al. |
| 7,863,487 B2 | 1/2011 | Eisenschmid et al. |
| 7,943,801 B2 | 5/2011 | Choi et al. |
| 8,178,729 B2 | 5/2012 | Karvinen et al. |
| 8,513,469 B2 * | 8/2013 | Brammer ................ C07C 45/50 568/454 |
| 8,741,173 B2 | 6/2014 | Brammer et al. |
| 9,687,837 B1 * | 6/2017 | Devon .................. C07F 9/5027 |
| 2007/0123735 A1 | 5/2007 | Jeon et al. |
| 2012/0253080 A1 | 10/2012 | Eisenschmid et al. |

FOREIGN PATENT DOCUMENTS

| | | |
|---|---|---|
| CN | 1986055 A | 6/2007 |
| CN | 101288852 A | 10/2008 |
| CN | 102911021 A | 2/2013 |
| CN | 103990495 A | 8/2014 |
| CN | 104058944 A | 9/2014 |
| CN | 106083551 A | 11/2016 |
| CN | 106824282 A | 6/2017 |
| EP | 0073398 A1 | 3/1983 |
| EP | 0839787 A1 | 5/1998 |
| RU | 2354642 C2 | 5/2009 |

(Continued)

OTHER PUBLICATIONS

M. Matsumoto and T. Musuhiko, Rhodium-catalyzed low pressure hydroformylation of substituted terminal olefins. Role of bis(diphenylphosphino)alkane in combination with excess triphenylphosphine, Journal of Molecular Catalysis, 1982, pp. 195-207, vol. 16.

M. Matsumoto and T. Musuhiko, Reinvestigation of atmospheric hydroformylation of 1-octene catalyzed by a rhodium complex. Some advantages given by added bis(diphenylphosphino)alkane, Journal of Molecular Catalysis, 1982, pp. 209-216, vol. 16.

O.R. Hughes and J.D. Unruh, Hydroformylation Catalyzed by Rhodium Complexes with Diphosphine Ligands, Journal of Molecular Catalysis, 1981, pp. 71-83, vol. 12.

Yu, et al, Synthesis and Application of Tetraphosphane Ligands in Rhodium-Catalyzed Hydroformylation of Terminal Olefins: High Regioselectivity at High Temperature,Chemistry—A European Journal, 2010, vol. 16, No. 16, pp. 4938-4940.

(Continued)

*Primary Examiner* — Sikarl A Witherspoon

(57) ABSTRACT

The present invention relates to methods for slowing deactivation of a catalyst and/or slowing tetraphosphine ligand usage in a hydroformylation process. In one aspect, a method comprises (a) contacting an olefin with carbon monoxide, hydrogen and a catalyst, the catalyst comprising (A) a transition metal, (B) a tetraphosphine having the structure described herein, and, optionally, (C) a monophosphine having the structure described herein, the contacting conducted in one or more reaction zones and at hydroformylation conditions; and (b) adding additional monophosphine having the structure described herein to a reaction zone.

10 Claims, No Drawings

(56) References Cited

FOREIGN PATENT DOCUMENTS

| RU | 2562971 C1 | 9/2015 |
| WO | 2010117391 A1 | 10/2010 |
| WO | 2012047514 A1 | 4/2012 |
| WO | 2014035673 A1 | 3/2014 |

OTHER PUBLICATIONS

Zhang, Development and Applications of Phosphorus Ligands in Rhodium-Catalyzed Hydroformylation and Hydrogenation, Dissertion Penn State University, 2011, pp. 119-164.
PCT/US2019/030571, International Search Report and Written Opinion dated Oct. 10, 2019.
PCT/US2019/030571, International Preliminary Report on Patentability dated Dec. 1, 2020.

* cited by examiner

METHODS FOR SLOWING DEACTIVATION OF A CATALYST AND/OR SLOWING TETRAPHOSPHINE LIGAND USAGE IN HYDROFORMYLATION PROCESSES

FIELD

The present invention relates to methods of slowing deactivation of a catalyst and/or slowing tetraphosphine ligand usage in hydroformylation process.

BACKGROUND

It is known in the art that aldehydes may be readily produced by reacting an olefinically unsaturated compound with carbon monoxide and hydrogen in the presence of a solubilized rhodium-triorganophosphorous ligand complex catalyst and that a preferred type of such processes involves continuous hydroformylation. For example, U.S. Pat. No. 3,527,809 discloses the hydroformylation of alpha-olefins to produce aldehydes at low temperatures and pressures. The process employs certain rhodium complexes to effectively catalyze, under a defined set of variables in the presence of select triorganophosphorous ligands, the hydroformylation of olefins with hydrogen and carbon monoxide.

Among the catalysts described in U.S. Pat. No. 3,527,809 are compounds containing rhodium and triarylphosphorous ligands, in particular triarylphosphine ligands exemplified by triphenylphosphine ("TPP"). Commercial hydroformylation processes have successfully employed the rhodium-TPP catalyst for decades, and a key aspect of operation is the use of a large excess of TPP relative to rhodium. For example, industrial propylene hydroformylation processes often operate with TPP concentrations of 10-12 weight percent based on the total mass of the reaction fluid. Such high concentrations of TPP are used to achieve the desired product regioselectivity and to enhance catalyst stability.

Over time, hydroformylation catalysts tend to deactivate due to a plurality of causes including rhodium clustering or the presence of inhibitory compounds. Steps may be taken to maintain production targets, such as increasing the rhodium concentration, raising reaction temperatures, or catalyst rejuvenation treatments such as the procedure taught in U.S. Pat. No. 5,237,106. Despite these efforts, catalysts eventually reach a point where deactivation has rendered them nonviable for commercial use. These "end of life" catalysts must be removed from the process, sent off for precious metal recovery (PMR), and replaced with fresh charges of rhodium and ligand(s). The costs associated with PMR, replacing the entire rhodium and ligand inventories and the loss of production during the catalyst change can be significant.

Hydroformylation processes employing C3 and higher olefins produce a mixture of linear (normal) and branched (iso) aldehyde; the regioselectivity is typically expressed as the normal to isoaldehyde ratio (N:I). It is well known that catalysts capable of producing an N:I in excess of about 10-12 are comprised of chelating ligands containing at least two phosphorous moieties (see for example "Rhodium Catalyzed Hydroformylation, Kluwer Academic Publishers, 2000). Specific examples include but are not limited to tetraphosphine ligands such as those described in U.S. Pat. No. 7,531,698.

Such chelating ligands are typically prepared via custom syntheses which increases their cost. Chelating ligands are known to degrade during continuous operation due to oxidation, hydrolysis, or rhodium-promoted side reactions. Because the hydroformylation rate and product regioselectivity will suffer if the chelating ligand concentration falls too low, it is common practice to periodically replenish these compounds to maintain the desired performance. The rate at which the chelating ligand must be added to the system to maintain the target concentration ("ligand usage rate") is a key economic factor for processes employing these expensive compounds.

It would be desirable to have a method for slowing the deactivation of catalysts and/or the ligand usage rate for high N:I hydroformylation processes.

SUMMARY

The present invention relates for slowing the deactivation of a catalyst and/or the tetraphosphine ligand usage rate in a hydroformylation process. For example, according to some embodiments, it has surprisingly been discovered that the addition of certain monophosphines to a reaction zone can slow the decline in hydroformylation rate and/or slow the usage rate of a chelating tetraphosphine ligand.

In one aspect, a method for slowing deactivation of a catalyst and/or slowing tetraphosphine ligand usage in a hydroformylation process comprises:

(a) contacting an olefin with carbon monoxide, hydrogen and a catalyst, the catalyst comprising (A) a transition metal; (B) a tetraphosphine having the following structure:

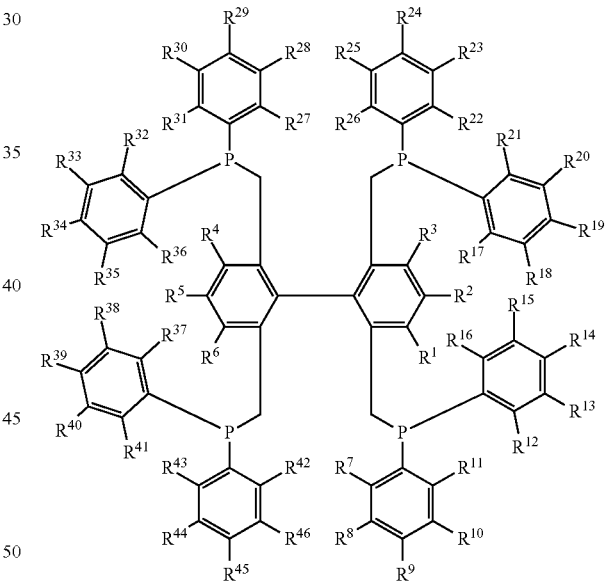

wherein each P is a phosphorous atom, and each of $R^1$-$R^{46}$ are independently hydrogen, a C1 to C8 alkyl group, an aryl group, an alkaryl group, or a halogen, and, optionally, (C) a monophosphine having the following structure:

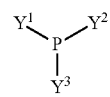

wherein P is a phosphorous atom, and each of $Y^1$-$Y^3$ are independently an aryl group, an alkaryl group, a cycloalkyl group, a benzyl group, a C3 to C8 alkyl group, an alkoxyl group of 1-8 carbons, an aryloxy group, or a halogen, the contacting conducted in one or more reaction zones and at hydroformylation conditions; and (b) adding additional monophosphine having the above structure to a reaction zone. In some embodiments, the transition metal is rhodium and the monophosphine is triphenylphosphine.

These and other embodiments are discussed in more detail in the Detailed Description below.

DETAILED DESCRIPTION

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible sub-ranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "ligand degradation" and "ligand decomposition" are used interchangeably and are contemplated to comprise a chemical transformation of either monophosphine or tetraphosphine charged to the reaction fluid.

The term "tetraphosphine ligand usage" is contemplated to comprise the amount of tetraphosphine that is consumed by the hydroformylation process (e.g., by ligand degradation) over time. For example, accounting for the tetraphosphine which is added to the hydroformylation process, and periodically measuring tetraphosphine concentration in the reaction fluid (using the HPLC method described in the Examples below) will allow the amount of tetraphosphine being consumed by the process to be calculated.

The terms "deactivation" and "catalyst deactivation" are used interchangeably and are contemplated to comprise a decline in the hydroformylation rate over time. Persons of ordinary skill in the art will understand that the hydroformylation rate can be determined using a variety of techniques. As one example, the hydroformylation rate can be determined by taking at least two measurements at comparable process conditions (e.g. similar rhodium concentration, reaction temperature, gas partial pressures, etc.) over a period of time. For example, the rate of aldehyde production (e.g., pounds of product per hour measured by determining the amount of aldehyde in a stream leaving the reactor at a constant flow using gas chromatography) at comparable process conditions is measured regularly over a period of weeks. A decline in the amount of aldehyde being produced would indicate catalyst deactivation.

The terms "reaction fluid," "reaction medium" and "catalyst solution" are used interchangeably herein, and may include, but are not limited to, a mixture comprising: (a) a transition metal-monophosphine complex catalyst (e.g., a rhodium-triphenylphosphine complex catalyst), (b) a transition metal-tetraphosphine complex catalyst (e.g., a rhodium-tetraphosphine complex catalyst), (c) free monophosphine (e.g., triphenylphospine), (d) free tetraphosphine, (e) aldehyde products formed in the reaction, (f) unreacted reactants, (g) a solvent for said transition metal complex catalysts and said free phosphine ligands, and, optionally (h) monophosphine ligand and tetraphosphine ligand degradation products. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a fluid in an external cooler, and (g) ligand degradation products.

The term "ligand degradation products" is contemplated to include, but is not limited to any and all compounds resulting from one or more chemical transformations of at least one of the tetraphosphine and/or monophosphine molecules charged to the reaction fluid. Such compounds may include but are not limited to triphosphine or diphosphine compounds derived from rhodium-promoted cleavage of the parent tetraphosphine as well as the smaller phosphine moieties resulting from said cleavage side reactions. Ligand degradation products are also contemplated to include alkyl-diarylphosphines which are known to be present in rhodium-triarylphosphine hydroformylation catalyst solutions (see, for example, U.S. Pat. No. 4,297,239, col. 5). Ligand degradation products are additionally contemplated to include any and all compounds which result from oxidation of phosphine moieties. For example, ligand degradation products may comprise phosphine oxides derived from monophosphine introduced to the process, from partial or complete oxidation of tetraphosphine introduced to the process, or from the oxidation of phosphine compounds resulting from rhodium-promoted side reactions (e.g. oxidation of triphosphine compounds derived from the parent tetraphosphine).

As used herein the terms "tetradentate phosphine" and "tetraphosphine" are used interchangeably and are contemplated to comprise compounds containing four phosphine atoms each one of which is bound to three carbon atoms.

As used herein the terms "monodentate phosphine" and "monophosphine" are used interchangeably and comprise compounds which contain a single phosphine atom bound to three carbon atoms.

As used herein the terms "rhodium complex", "rhodium complex catalyst", and "catalyst complex" are used interchangeably and are contemplated to comprise at least one rhodium atom with ligands bound or coordinated via electron interaction. Examples of such ligands include but are not limited to monophosphine, tetradentate phosphine, carbon monoxide, propylene and hydrogen.

As used herein, the term "free" phosphine is contemplated to comprise monophosphine or tetraphosphine molecules that are not bound or coordinated to rhodium.

In general, the present invention is directed to methods for slowing deactivation of a catalyst and/or slowing tetraphosphine ligand usage in a hydroformylation process. The catalyst includes a transition metal (e.g., rhodium) and a tetraphosphine ligand.

In one aspect, a method for slowing deactivation of a catalyst and/or slowing tetraphosphine ligand usage in a hydroformylation process comprises:

(a) contacting an olefin with carbon monoxide, hydrogen and a catalyst, the catalyst comprising (A) a transition metal; (B) a tetraphosphine having the following structure:

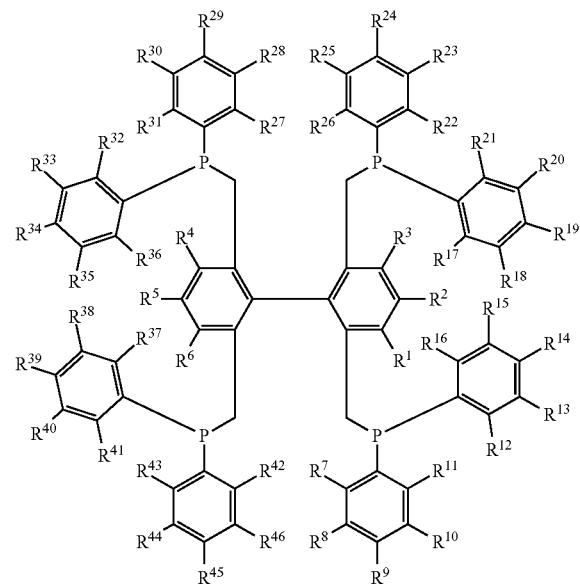

wherein each P is a phosphorous atom, and each of $R^1$-$R^{46}$ are independently hydrogen, a C1 to C8 alkyl group, an aryl group, an alkaryl group, or a halogen, and, optionally, (C) a monophosphine having the following structure:

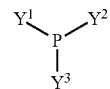

wherein P is a phosphorous atom, and each of $Y^1$-$Y^3$ are independently an aryl group, an alkaryl group, a cycloalkyl group, a benzyl group, a C3 to C8 alkyl group, an alkoxyl group of 1-8 carbons, an aryloxy group, or a halogen, the contacting conducted in one or more reaction zones and at hydroformylation conditions; and (b) adding additional monophosphine having the above structure to a reaction zone. The transition metal, in some embodiments, comprises rhodium. In some embodiments, the olefin is propylene. In some embodiments, the amount of monophosphine added is at least 40 moles of phosphine per mole of transition metal. The amount of monophosphine added to the reactor zone, in some embodiments, is greater than 1.5 weight percent of the reaction fluid in the reaction zone based on the total weight of the reaction fluid in the reaction zone.

The monophosphine, in some embodiments, is one or more of the following: triphenylphosphine, tris(o-tolyl) phosphine, trinaphthylphosphine, tri(p-methoxyphenyl) phosphine, tri(m-chlorophenyl)-phosphine, tribenzylphosphine, tricyclohexylphosphine, dicyclohexylphenylphosphine, cyclohexyldiphenylphosphine, and trioctylphosphine. The monophosphine is triphenylphosphine in some embodiments. In some embodiments, the monophosphine is a bulky monophosphine. In some embodiments, the catalyst comprises a mixture of different species of monophosphines.

In some embodiments, each of $R^1$-$R^{46}$ in the structure for the tetraphosphine are hydrogen. In some embodiments the catalyst comprises one or more of the following tetraphosphines:

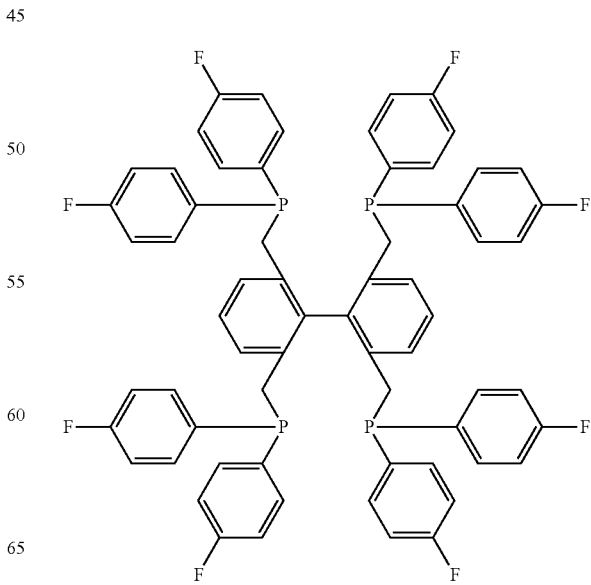

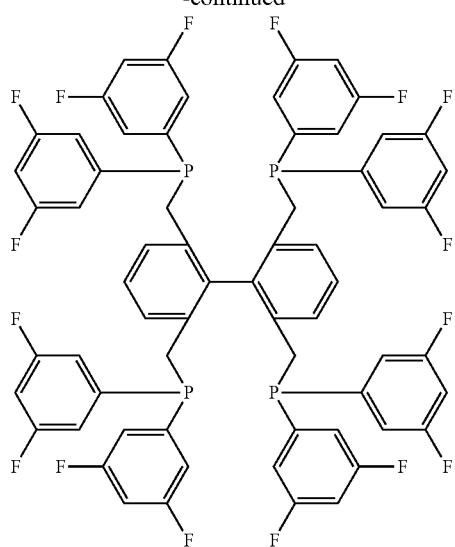
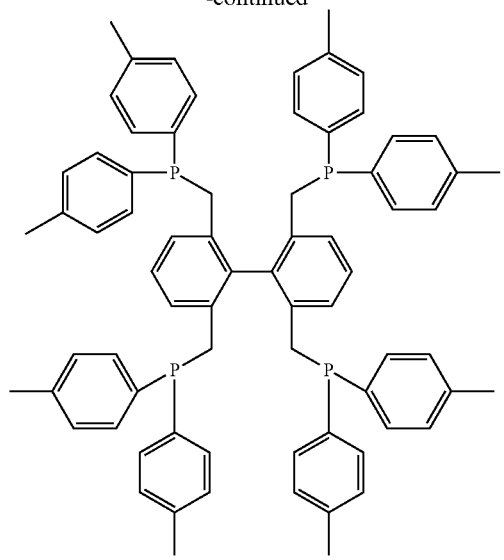
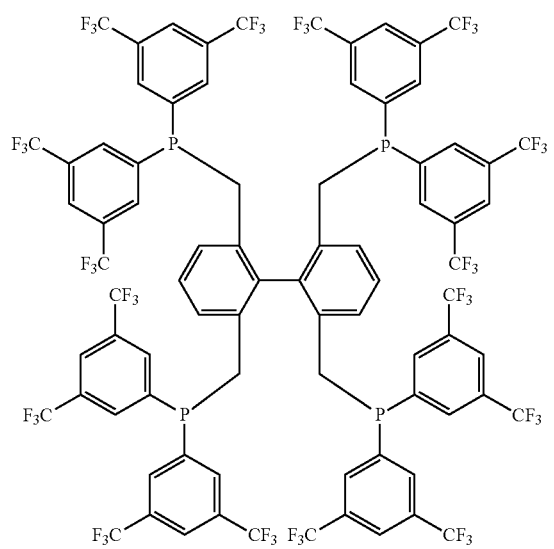
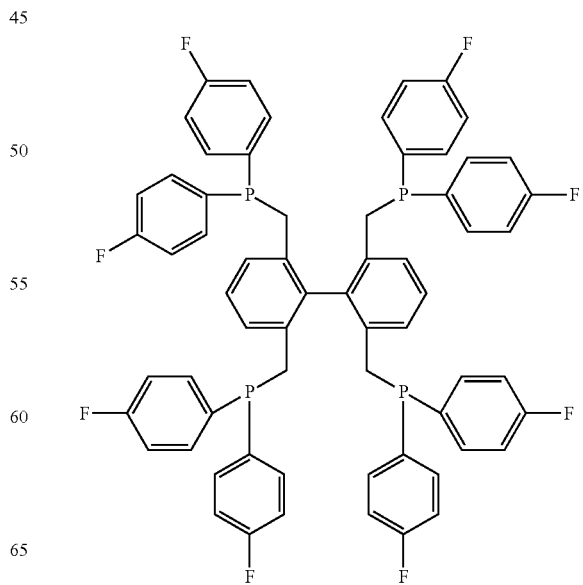

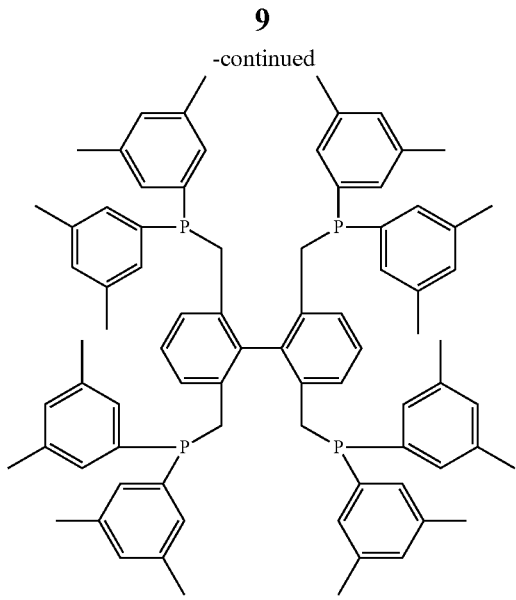

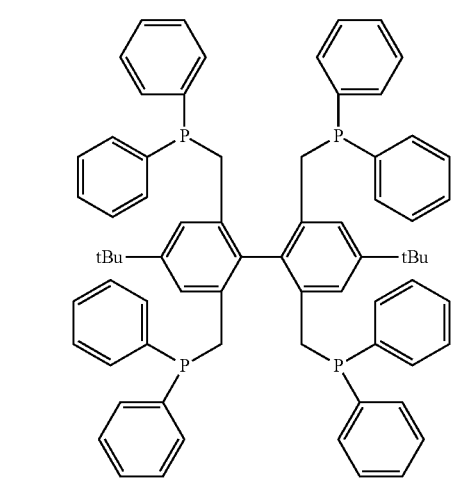

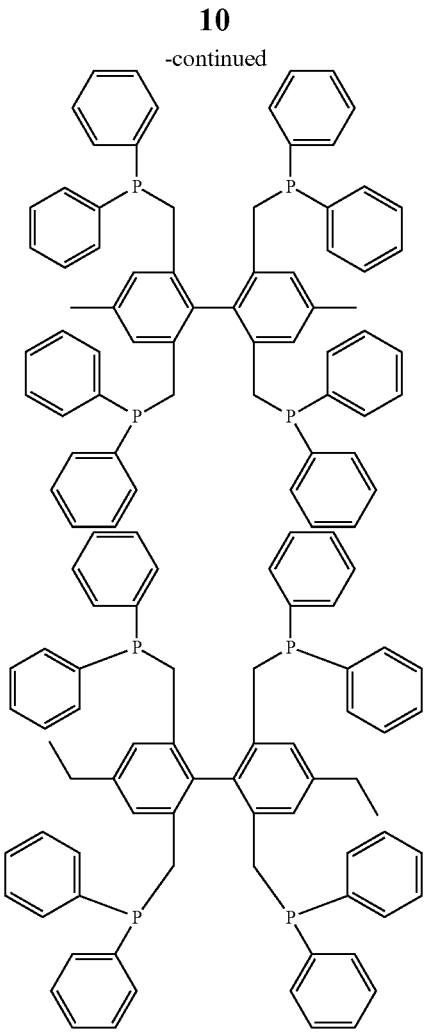

In some embodiments, the transition metal comprises rhodium, the monophosphine is triphenylphospine, each of $R^1$-$R^{46}$ are hydrogen, and the olefin comprises propylene.

In some embodiments, the decline in hydroformylation rate over time is less than in a process under identical conditions, with the exception of the absence of monophosphine. In some embodiments, the rate of tetraphosphine ligand usage in the hydroformylation process is less than in a hydroformylation process under identical conditions, with the exception of the absence of monophosphine.

Hydrogen and carbon monoxide may be obtained from any suitable source, including petroleum cracking and refinery operations.

Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications. Syngas mixtures are a preferred source of hydrogen and CO.

The olefinic starting material reactants that may be employed in the hydroformylation reactions encompassed by of this invention can be terminally or internally unsaturated and be of straight-chain, branched-chain or cyclic structure. Such olefins can contain from 2 to 20 carbon atoms and may contain one or more ethylenic unsaturated groups. Moreover, such olefins may contain groups or substituents which do not essentially adversely interfere with the hydroformylation process such as carbonyl, carbonyloxy, oxy, hydroxy, oxycarbonyl, halogen, alkoxy, aryl, alkyl, haloalkyl, and the like. Illustrative olefinic unsaturated compounds include alpha olefins, internal olefins, alkyl alkenoates, alkenyl alkanoates, alkenyl alkyl ethers, alkenols, and the like, e.g. ethylene, propylene, 1-butene, 1-pentene, 1-hexene, 1-octene, 1-decene, 1,-dodecene, 1-octadecene, 2-butene, isobutylene, 2-methylbutene, 2-hexene, 3-hexene, 2-heptene, cyclohexene, propylene dimers, propylene trimers, propylene tetramers, butene dimers, butene trimers, 2-ethyl-1-hexene, styrene, 3-phenyl-1-propene, 1,4-hexadiene, 1,7-octadiene, 3-cyclohexyl-1-butene, and the like. Of course, it is understood that mixtures of different olefinic starting materials can be employed, if desired. Embodiments of the present invention can be particularly useful in the hydroformylation of C3 and higher olefins. Thus, in some embodiments, the olefinic unsaturated starting materials are alpha olefins containing from 3 to 20 carbon atoms, and internal olefins containing from 3 to 20 carbon atoms as well as starting material mixtures of such alpha olefins and internal olefins.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,830 and 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

The catalyst used in methods of the present invention comprises a transition metal and a tetraphosphine. In certain particularly useful embodiments, the catalyst comprises rhodium and a tetraphosphine. The most desirable catalyst is free of metal-bound halogens such as chlorine, and contains hydrogen, carbon monoxide and tetraphosphine complexed with rhodium metal to produce a catalyst soluble in the aforementioned liquid phase and stable under the conditions of the reaction.

The transition metal can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with preferred metals being rhodium, cobalt, iridium and ruthenium, more preferably rhodium, cobalt and ruthenium, especially rhodium.

The number of available coordination sites on such metals is well known in the art. Thus the catalytic species, which may comprise a complex catalyst mixture, may comprise monomeric, dimeric or higher nuclearity forms, which are preferably characterized by at least one organophosphine-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphine ligands in view of the carbon monoxide and hydrogen gas employed by the hydroformylation reaction.

In certain preferred embodiments, the transition metal is rhodium. Rhodium can be introduced into the liquid phase as a preformed catalyst, e.g., a stable crystalline solid, rhodium hydridocarbonyl-tris(triphenyl phosphine), $RhH(CO)(PPh_3)_3$. The rhodium can be introduced to the liquid body as a precursor form which is converted in situ into the catalyst. Examples of such precursor form are rhodium carbonyl triphenylphosphine acetylacetonate, $Rh_2O_3$, $Rh_4(CO)_{12}$, $Rh_6(CO)_{16}$, and rhodium dicarbonyl acetylacetonate. Both the catalyst compounds which will provide active species in the reaction medium and their preparation are known by the art, see Brown et al., *Journal of the Chemical Society*, 1970, pp. 2753-2764.

In general the optimum catalyst concentration depends on the concentration of the alpha-olefin, such as propylene. For example, the higher the propylene concentration the lower usually will be the catalyst concentration needed to achieve a given conversion rate to aldehyde products in a given size of reactor. Recognizing that partial pressures and concentration are related, the use of higher propylene partial pressure leads to an increased proportion of propylene in the "off gas" from the liquid body. Since it may be necessary to purge part of the gas stream from the product recovery zone before recycle to the liquid body in order to remove a portion of the propane which may be present, the higher the propylene content of the "off gas" is, the more propylene that will be lost in the propane purge stream. Thus it is necessary to balance the economic value of the propylene lost in the propane purge stream against the capital savings associated with lower catalyst concentration.

The rhodium complex catalysts may be in homogeneous or heterogeneous form. For instance, preformed rhodium hydrido-carbonyl-phosphine ligand catalysts may be prepared and introduced into a hydroformylation reaction mixture. More preferably, the rhodium-phosphine ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the tetraphosphine for the in situ formation of the active catalyst. In a preferred embodiment, rhodium dicarbonyl acetylacetonate is employed as a rhodium precursor and combined with tetraphosphine in a solvent and introduced into the reactor along with syn gas for the in situ formation of the active catalyst. Additional tetraphosphine may be added as necessary to achieve and maintain the desired concentrations. In any event, it is sufficient that carbon monoxide, hydrogen, and tetraphosphine are all ligands that are capable of being complexed with the metal and that an active metal-ligand catalyst is present in the reaction mixture under the conditions used in the hydroformylation reaction.

In some embodiments, a catalyst composition is formed in a mix tank by combining the rhodium catalyst precursor with tetraphosphine.

The amount of rhodium complex catalyst present in the reaction fluid need only be that minimum amount necessary to produce the desired production rate. In general, rhodium concentrations in the range of from 150 ppmw to 1200 ppmw, calculated as free metal in the reaction fluid in a hydroformylation reactor, should be sufficient for most processes, while it is generally preferred to employ from 150 to 800 ppmw of metal, and more preferably from 150 to 500 ppmw of rhodium.

The amount of tetraphosphine in the catalyst composition (whether formed entirely in a mix tank or formed in the reactor) is at least 1 mole of tetraphosphine per mole of transition metal (rhodium). In some embodiments, the amount of tetraphosphine in the catalyst composition (whether formed entirely in a mix tank or formed in the reactor) is from 1 to 10 moles of tetraphosphine per mole of transition metal (rhodium). The amount of moles of tetraphosphine is measured by high performance liquid chromatography (HPLC) as described in the Examples. The amount of moles of rhodium is measured by atomic absorption.

For commercial operations, ligand concentrations must be maintained by periodic or continuous additions. To do so, the concentrations of ligands in the reaction fluid are routinely measured by one or more analytical techniques; high performance liquid chromatography (HPLC) is typically preferred. Unless otherwise indicated herein, when referring to the amount of ligand in a reaction, the ligand concentration is determined by HPLC as described in the Examples. Ligand concentrations in such analyses are often reported as weight percent; thus it is often convenient to use these units for continuous operation. In some embodiments, the amount tetraphosphine in the reaction fluid in a reactor of a hydroformylation process is greater than or equal to 0.06 weight percent based on the total weight of the reaction fluid in the reactor. In some embodiments, the amount of tetraphosphine in the reaction fluid in a reactor of a hydroformylation process is from 0.1 to 9 weight percent based on the total weight of the reaction fluid in the reactor. In some embodiments wherein $R^1$-$R^{46}$ in the tetraphosphine shown above are each hydrogen, the amount of tetraphosphine in the reaction fluid in a reactor of a hydroformylation process is from 0.1 to 4 weight percent based on the total weight of the reaction fluid in the reactor.

By way of illustration, a preferred catalyst precursor composition consists essentially of a solubilized rhodium complex precursor, tetraphosphine, and a solvent. The tetraphosphine will readily replace one of the carbonyl ligands of the rhodium acetylacetonate complex precursor as witnessed by the evolution of carbon monoxide gas. Upon introduction of the catalyst precursor composition to the reactor, additional tetraphosphine may optionally then be added to achieve the target concentrations within the reaction fluid.

Accordingly, the rhodium-ligand complex catalysts in the reaction fluid of a hydroformylation reactor advantageously comprise rhodium complexed with carbon monoxide and tetraphosphine. In one embodiment, mixtures of rhodium-ligand complexes are employed. For example, the catalyst additionally comprises rhodium complexed with carbon monoxide and tetraphosphine in a chelated and/or non-chelated fashion.

In addition to the rhodium complex catalyst, free monophosphine (i.e., monophosphine that is not complexed with the metal) may also be present in the reaction fluid, and may also be present in a catalyst composition prior to being provided to a reactor depending on the particular composition. The significance of free ligand is taught in U.S. Pat. No. 3,527,809, GB 1,338,225, and Brown et al., supra., pages 2759 and 2761. In some embodiments, the hydroformylation process of this invention may involve from 1 weight percent or higher of free monophosphine in the reaction medium. The reaction fluid may also contain free tetradentate phosphine. In some such embodiments, the concentration of free tetradentate phosphine may range from 0.1 to 10 moles per mole of rhodium.

The tetraphosphine compounds that may serve as the ligands in embodiments of the present invention are compounds of Formula I:

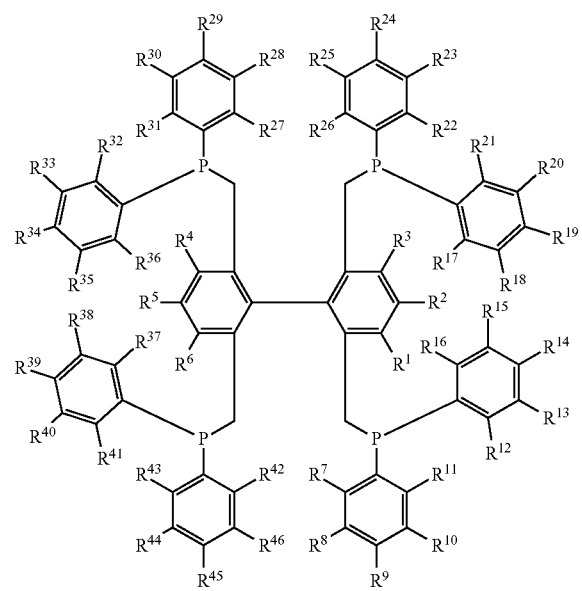

Formula I wherein each P is a phosphorous atom, and each of $R^1$-$R^{46}$ are independently hydrogen, a C1 to C8 alkyl group, an aryl group, an alkaryl group, a haloalkyl group, or a halogen. In a preferred embodiment, each of $R^1$-$R^{46}$ is hydrogen. Other examples of tetraphosphines that can be used in some embodiments are described elsewhere in the present specification.

Mixtures of tetraphosphines can be used in some embodiments.

Hydroformylation processes, and conditions for their operation, are well known. In a typical embodiment, an olefin (e.g., propylene) is hydroformylated in a continuous or semi-continuous fashion, with the product being separated in a separation zone, and the concentrated catalyst solution being recycled back into one or more reactors. The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. Nos. 5,430,194 and 5,681,473, or by the more conventional and preferred method of distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing retentate of such membrane separation or recovered non-volatilized metal catalyst containing residue of such vaporization separation can be recycled, to the hydroformylation zone (reactor) in any conventional manner desired.

A typical hydroformylation reaction fluid utilizing a rhodium-tetraphosphine ligand complex contains at least some amount of four main ingredients or components, i.e., the aldehyde product a rhodium-tetraphosphine ligand complex catalyst, free tetraphosphine ligand, and a solvent for said catalysts and said free ligands. The hydroformylation reaction mixture compositions can and normally will contain additional ingredients such as those that have either been deliberately employed in the hydroformylation process or formed in situ during said process. Examples of such additional ingredients include unreacted olefin starting material, carbon monoxide and hydrogen gases, and in situ formed by-products, ligand degradation compounds, and high boiling liquid aldehyde condensation by-products, as well as other inert co-solvent type materials or hydrocarbon additives, if employed.

The hydroformylation reaction conditions employed may vary. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1.

In general, the hydroformylation process may be conducted at any operable reaction temperature. Advantageously, the hydroformylation process is conducted at a reaction temperature from −25° C. to 200° C., preferably from 50° C. to 120° C.

The hydroformylation process may be carried out using one or more suitable reactors such as, for example, a continuous stirred tank reactor (CSTR), venturi reactor, bubble column reactor, or a slurry reactor. The optimum size and shape of the reactor will depend on the type of reactor used. The reaction zone employed may be a single vessel or may comprise two or more discrete vessels. The separation zone employed may be a single vessel or may comprise two or more discrete vessels. The reaction zone(s) and separation zone(s) employed herein may exist in the same vessel or in different vessels. For example, reactive separation techniques such as reactive distillation, and reactive membrane separation may occur in the reaction zone(s).

The hydroformylation process can be conducted with recycle of unconsumed starting materials if desired. The reaction can be conducted in a single reaction zone or in a plurality of reaction zones, and in series or in parallel. The reaction steps may be effected by the incremental addition of one of the starting materials to the other. Also, the reaction steps can be combined by the joint addition of the starting materials. The starting materials may be added to each or all of the reaction zones in series. When complete conversion is not desired or not obtainable, the starting materials can be separated from the product, for example by distillation, and the starting materials then recycled back into the reaction zone.

The hydroformylation process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In one embodiment, the hydroformylation process useful in this invention may be carried out in a multistaged reactor such as described, for example, in U.S. Pat. No. 5,728,893. Such multistaged reactors can be designed with internal, physical barriers that create more than one theoretical reactive stage per vessel.

As discussed herein, in a hydroformylation process over time, there is some catalyst deactivation and/or ligand degradation. Catalyst deactivation and/or ligand degradation can advantageously be reduced in such hydroformylation processes using tetraphospine ligands by adding a monophosphine (as described further herein) to the reaction zone.

The monophosphine compounds that may be added to the reaction zone according to embodiments of the present invention are compounds of Formula II:

(Formula II)

wherein P is a phosphorous atom, and each of $Y^1$-$Y^3$ are independently an aryl group, an alkaryl group, a cycloalkyl group, a benzyl group, a C3 to C8 alkyl group, an alkoxyl group of 1-8 carbons, an aryloxy group, or a halogen.

Illustrative examples include but are not limited to triphenylphosphine, tris(o-tolyl)phosphine, trinaphthylphosphine, tri(p-methoxyphenyl) phosphine, tri(m-chlorophenyl)-phosphine, tribenzylphosphine, tricyclohexylphosphine, dicyclohexylphenylphosphine, cyclohexyldiphenylphosphine, trioctylphosphine, and the like.

In some embodiments, the monophosphine is a bulky or sterically hindered monophosphine. For the purposes of the invention, a "bulky" or "sterically hindered" ligand is a ligand with a Tolman steric parameter of 135 to 190°. For example, in some such embodiments, $Y^1$-$Y^3$ in Formula II can independently be a substituted or unsubstituted C3 to C8 alkyl, a substituted or unsubstituted C5 to C8 cycloalkyl group, or a substituted or unsubstituted C6 to C12 aryl group. Representative preferred bulky monophosphines include those described in U.S. Pat. Nos. 4,283,562 and 5,741,945 (e.g., col. 10, line 57 through col. 13, line 39).

Mixtures of monophosphines can be used in some embodiments.

The amount of monophosphine that can be added to a reaction zone, in some embodiments, is at least 40 moles of monophosphine per mole of transition metal (rhodium). In some embodiments, the amount of monophosphine added to a reaction zone is from 40 to 350 moles of monophosphine per mole of transition metal (rhodium).

While tetraphosphine ligand can conceivably degrade to one or more monophosphine compounds, the amount of monophosphine to be added to the reaction fluid according to embodiments of the present invention are much greater than would be expected to potentially appear through degradation. In other words, the vast majority of the monophosphine in the reaction fluid is added (e.g., not derived from the tetraphosphine present in the catalyst composition or reaction fluid).

For commercial operations, ligand concentrations must be maintained by periodic or continuous additions. To do so, the concentrations of ligands in the reaction fluid are routinely measured by one or more analytical techniques; high performance liquid chromatography (HPLC) is typically preferred. Unless otherwise indicated herein, when referring to the amount of monophosphine ligand in a reaction zone, the ligand concentration is determined by HPLC as described in the Examples. Ligand concentrations in such analyses are often reported as weight percent; thus it is often convenient to use these units for continuous operation. In some embodiments, the amount of monophosphine added to the reactor is greater than 1.5 weight percent of the reaction fluid in the reactor based on the total weight of the reaction fluid in the reactor. In some embodiments, the amount of monophosphine added to the reactor is from 1.5 to 13 weight percent of the reaction fluid in the reactor on the total weight of the reaction fluid in the reactor.

The addition of monophosphine to the hydroformylation reactor utilizing the tetraphospine of Formula (I) (as discussed herein) advantageously reduces the decline in hydroformylation rate that would normally be expected, in some embodiments. That is, the decline in hydroformylation rate over time, when the specified monophosphine is added, is less than in a hydroformylation process under identical conditions, with the exception of the absence of monophosphine. This can advantageously facilitate the production of more aldehydes over time using the same amount of transition metal/tetraphosphine catalyst.

In some embodiments, the addition of monophosphine to the hydroformylation reactor utilizing the tetraphospine of Formula (I) (as discussed herein) advantageously reduces the rate of tetraphosphine ligand usage that would normally be expected. That is, the tetraphosphine used as the ligand would degrade at a lesser rate, when the specified monophosphine is added, than it would under identical conditions, with the exception of the absence of monophosphine. This can advantageously extend the useful life of the transition metal/tetraphosphine catalyst.

It is generally preferred to carry out the hydroformylation process in a continuous manner. Continuous hydroformylation processes are well known in the art. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990.

In one embodiment, the aldehyde product mixtures may be separated from the other components of the crude reaction mixtures in which the aldehyde mixtures are produced by any suitable method such as, for example, solvent extraction, crystallization, distillation, vaporization, wiped film evaporation, falling film evaporation, phase separation, filtration, or any combination thereof. It may be desired to remove the aldehyde products from the crude reaction mixture as they are formed through the use of trapping agents as described in WO 88/08835. One method for separating the aldehyde mixtures from the other components of the crude reaction mixtures is by membrane separation, which is described, for example in U.S. Pat. Nos. 5,430,194 and 5,681,473.

As indicated above, desired aldehydes may be recovered from the reaction mixtures. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may, if desired, any other volatile materials, e.g., unreacted olefin, together with any hydrogen and carbon monoxide dissolved in the liquid reaction after separation thereof from the condensed aldehyde product, e.g., by distillation in any conventional manner.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. In one embodiment, such aldehyde distillation takes place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g. vaporizer/separator, wherein the desired aldehyde product is distilled. In general, distillation pressures ranging from vacuum pressures on up to total gas pressure of 340 kPa should be sufficient for most purposes.

In one embodiment, flowing gases may be used in the separation zone to facilitate the aldehyde distillation. Such strip gas vaporizers are described for example in U.S. Pat. No. 8,404,903.

The increased concentrations, high temperatures, and low partial pressures that occur in the separation zone may negatively affect the catalyst, both in terms of catalyst deactivation and/or increased ligand usage. As described below in the Examples, an accelerated testing procedure, referred to herein as the block-in procedure, has been devised for demonstrating the impact of the separation zone on the catalyst in order to evaluate various embodiments.

Illustrative non-optically active aldehyde products of hydroformylation processes according to embodiments of the present invention will depend on the olefin used as a reactant and can include e.g., propionaldehyde, n-butyraldehyde, isobutyraldehyde, n-valeraldehyde, 2-methyl 1-butyraldehyde, hexanal, hydroxyhexanal, 2-methyl 1-heptanal, nonanal, 2-methyl-1-octanal, decanal, adipaldehyde, 2-methylglutaraldehyde, 2-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, 2-methyl 1-decanal, 3-propyl-1-undecanal, pentadecanal, 3-propyl-1-hexadecanal, eicosanal, 2-methyl-1-tricosanal, pentacosanal, 2-methyl-1-tetracosanal, nonacosanal, 2-methyl-1-octacosanal, hentriacontanal, and 2-methyl-1-triacontanal, and the like.

In some embodiments where propylene is the olefin that undergoes the hydroformylation reaction, the product is a mixture of n-butyraldehyde and 2-methylpropionaldehyde. As previously noted, the ratio of linear (N) to branched (I) isomers such as the n-butyraldehyde to 2-methylpropionaldehyde (isobutyraldehyde) ratio is conventionally described as the N:I ratio or N:I.

In one embodiment, the catalyst comprises rhodium, one or more equivalents of tetraphosphine, and triphenylphosphine (e.g. 1.5-12 wt. %). For example, a process utilizing a catalyst comprised of rhodium and tetraphosphine may choose to add triphenylphosphine to lower tetraphosphine ligand usage and catalyst deactivation.

Some embodiments of the invention will now be described in more detail in the following Examples.

EXAMPLES

All parts and percentages in the following examples are by weight unless otherwise indicated. The concentration of Ligand A is expressed as equivalents, based on moles of Ligand A per mole of rhodium. Pressures in the following examples are given as pounds per square inch gauge unless otherwise indicated. All manipulations such as preparation of catalyst solutions are done under inert atmosphere unless otherwise indicated. Comparative Experiments are not embodiments of the invention.

Gas compositions (mole %) are measured by gas chromatography (GC) and partial pressures are then calculated based on the total pressure using Raoult's law.

Free tetradentate phosphine concentration is measured by High Pressure Liquid Chromatography (HPLC). In order to prevent oxidation during analysis, the phosphines are derivatized to stable phosphine sulfides by mixing with a sulfur-saturated diluent (50:50 by volume acetonitrile:THF saturated with elemental sulfur).

External standard HPLC analyses are performed on an Agilent 1200 Infinity Series HPLC equipped with an UHPLC SB-C8 3.0 mm, 1.8 um guard column followed by a Zorbax SB-C8 analytical column (3.0×150 mm). Solvent gradient is 55% water with a balance of acetonitrile for 4 minutes; then adjusted to 20:80 water:acetonitrile for 22 minutes, and finally back to the original composition for the remainder of the 35 minute run. Solvent flow rate is 1.00 mL/min throughout, with the column temperature maintained at 40° C. Two microliters of sample is injected into the system; the multi-wavelength UV detector is set at 240 nm.

Preparation of Ligand A

The tetradentate phosphine compound Ligand A is used in these examples and is prepared as set forth below.

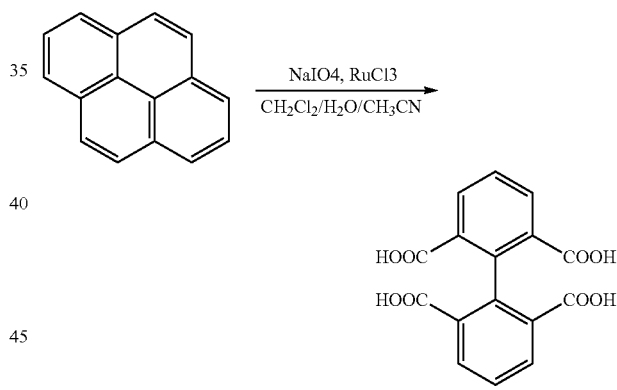

Synthesis of 1,1'-biphenyl-2-2',6,6'-tetracarboxylic acid. A 5 L jacketed reactor equipped with an overhead stirrer, bottom drain valve and water cooled condenser is charged with 1 L of methylene chloride and 50 g (0.247 mol) of pyrene. The mixture is stirred until the pyrene dissolves, after which 0.25 L of acetonitrile, 1.5 L of deionized water and 2.0 g of ruthenium (III) chloride are added. The resulting biphasic mixture is stirred vigorously and cooled to 18° C. by circulating cooling fluid through the jacket. Sodium periodate is then added in small portions (500 g total; 2.34 mol) over a period of 2.5 hours while maintaining a reactor temperature of 23-27° C. The reaction mixture which is initially brown in color quickly turns dark brown and finally brownish green. After stirring overnight (18 h) agitation is stopped and the layers allowed to separate. The lower layer is drained into a Buchner funnel to collect the crude green/brown solid product which is washed with methylene chloride (2×500 mL) and dried on the filter by flowing air. The solid is then returned to the reactor and refluxed with 1.5 L of acetone for 1 h. After cooling to room temperature, the yellow solution is drained into a Buchner funnel and the filtrate concentrated on a rotary evaporator leaving a yellow solid. The crude tetraacid product is dried in a vacuum oven at 70° C. overnight and used without further purification.

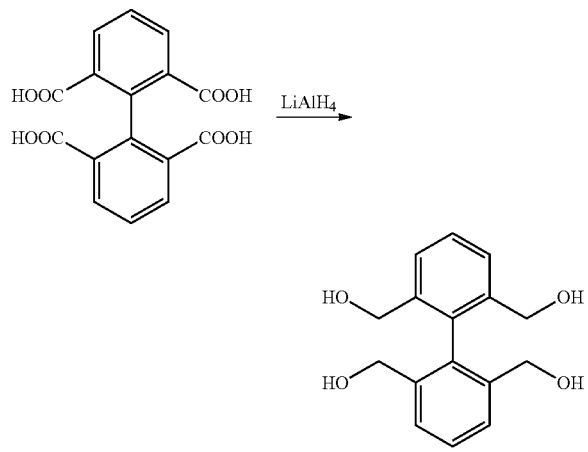

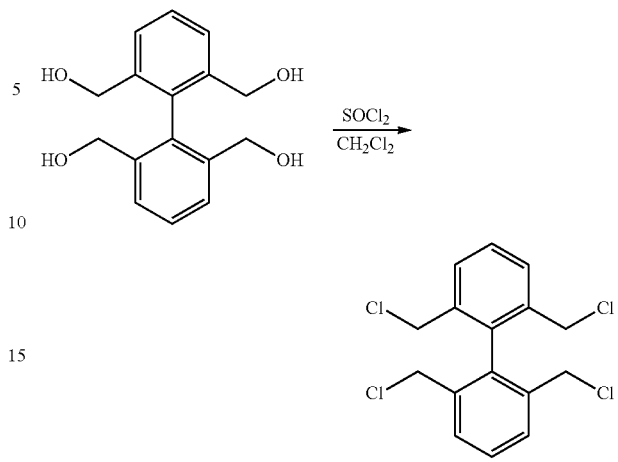

Synthesis of 1,1'-biphenyl-2,2',6,6'-tetramethanol. The 5 L reactor used in the previous step is dried and purged with nitrogen overnight. Crude 1,1'-biphenyl-2-2',6,6'-tetracarboxylic acid (50.0 g, 0.152 mol) is charged along with 1.5 L of THF under nitrogen. The resulting solution is stirred and cooled to 0° C. by circulating chilled fluid through the jacket of the reactor. A solution of lithium aluminum hydride in THF (1M; 666 mL; 0.665 mol) is then added via a peristaltic pump over 2 hours. During this time the mixture is stirred vigorously and the reactor temperature is maintained at 0-2° C.; for safety purposes a slow purge of nitrogen is applied to the reactor and the vent stream is passed through a condenser to sweep the reactor of evolved hydrogen. After the lithium aluminum hydride addition is complete, the reactor is stirred cold for an additional 15 minutes, then allowed to warm slowly to room temperature. After stirring at room temperature for 30 minutes, the reactor contents are heated to 65° C. and stirred overnight under a slow nitrogen purge. The next morning the reactor is cooled to 0° C. and quenched with 25 mL of water added slowly via the peristaltic pump, followed by 50 mL of 10% NaOH and 75 mL of water at 0-7° C. over a period of 1.5 hours. The quench procedure evolves hydrogen, and is therefore performed with a nitrogen sweep. The quenched solution is allowed to warm slowly to room temperature and then drained from the reactor into a Buchner funnel. The solids thus collected are washed with hot THF (3×300 mL). The volatiles are removed from the combined filtrate on a rotary evaporator to leave 35 g of a light yellow solid. The solids were dissolved in hot ethanol, filtered, and the solvent removed on a rotary evaporator. Drying overnight in a vacuum oven left 32.3 g of light yellow product (77.1% yield, ca. 97% purity). $^1$H NMR (400 MHz, DMSO). δ 7.46 (d, J=6.8 Hz, 4H), 7.39 (dd, J=8.6, 6.4 Hz, 2H), 4.99 (t, J=5.3 Hz, 4H), 3.94 (d, J=5.3 Hz, 8H) ppm. $^{13}$C NMR (400 MHz, DMSO) δ 139.3, 133.1, 127.3, 125.4, 60.4 ppm.

Synthesis of 2,2'6,6'-tetrakis(chloromethyl)-1,1'-biphenyl. The 5 L reactor is dried and purged with nitrogen overnight and then charged with 1,1'-biphenyl-2,2',6,6'-tetramethanol (45 g; 0.164 mol), methylene chloride (450 mL) and dimethylformamide (1 mL). The resulting yellow solution is stirred and cooled to 0° C. Thionyl chloride (1,071 g, 9.01 mol) is then added slowly via peristaltic pump over a 2 hour period, keeping the reactor temperature near 0° C.; during the addition the reactor is swept with nitrogen to remove the HCl and $SO_2$ which are generated, with the off gases passed through a water scrubber. The reaction solution is then allowed to warm to room temperature and stir for 30 minutes before heating to reflux (ca. 45° C.) overnight. The next day, the solution was cooled to 15° C. and discharged from the reactor. The methylene chloride was removed by distillation at atmospheric pressure, and the residual thionyl chloride removed by vacuum distillation. The resulting residue was dried first on a rotary evaporator followed by drying in a vacuum oven at 60° C. overnight to leave 58.1 g of yellow solid. (100% yield, ca. 95% purity). $^1$H NMR (400 MHz CDCl2) δ 7.66-7.60 (m, 4H), 7.56 (dd, J=8.8, 6.4 Hz, 2H), 4.28 (s, 8H) ppm. $^{13}$C NMR (400 MHz, CDCl2) δ 136.9, 135.5, 131.3, 130.3, 45.0 ppm.

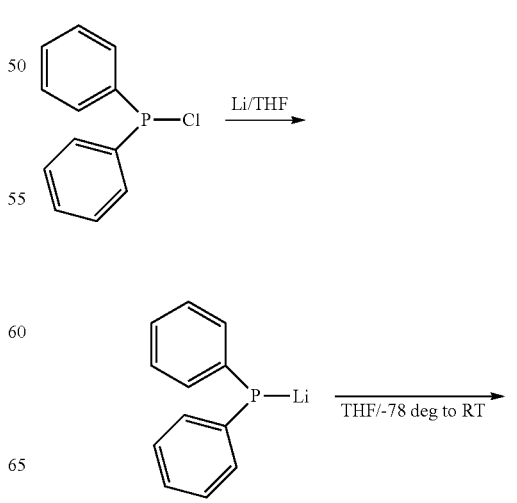

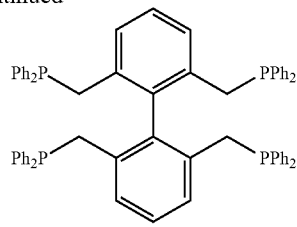

Synthesis of (biphenyl-2,2',6,6'-tetramethanediyl)tetrakis(diphenylphosphane) (Ligand A). Lithium wire (2.1 g, 300 mmol) is cut into small pieces and charged into a 250 mL flask in a dry box along with anhydrous THF (130 mL). The suspended solution is transferred to a Schlenk line and chilled in an ice water bath under nitrogen. Chlorodiphenylphosphine (28.1 mL, 151.7 mmol) was added dropwise at 0° C. over a period of 50 minutes and then stirred an additional 30 minutes at 0° C. During this time the color changes from cloudy yellow to red. The solution was transferred to a dry box and stirred at room temperature overnight. The next morning the solution was cannula filtered into a clean, dry 500 mL round bottom flask, transferred to the Schlenk line and chilled to −78° C. A solution of 2,2'6,6'-tetrakis(chloromethyl)-1,1'-biphenyl (12.7 g, 37 mmol) in THF (60 mL) was added dropwise over 50 minutes, and then stirred cold for an additional 20 minutes. The solution is then allowed to warm slowly to room temperature, and then transferred to the dry box and stirred overnight. Degassed methylene chloride (300 mL) and water (150 mL) were then added, and the resulting mixture allowed to separate. The lower layer was transferred to a round bottom flask and concentrated on a rotary evaporator at 30° C. to leave a solution of crude product in THF. While heating this solution at 65° C. under flowing nitrogen, degassed ethanol (100 mL) is added slowly. White solid began precipitating during the ethanol addition. The mixture was then allowed to cool and placed in a refrigerator overnight; the resulting solids are collected the next day by filtering in the dry box, and washing with ethanol (2×50 mL). Drying under vacuum overnight leaves the desired product as a white powder (90% yield, 99% purity). $^{31}$P NMR (400 MHz, CDCl3) δ −14.5 ppm. $^{1}$H NMR (400 MHz, CDCl3) δ 7.30-7.17 (m, 40H), 6.91-6.82 (m, 2H), 6.72 (d, J=7.7 Hz, 4H), 3.21 (s, 8H) ppm. Ligand A, the tetraphosphine, has the following structure:

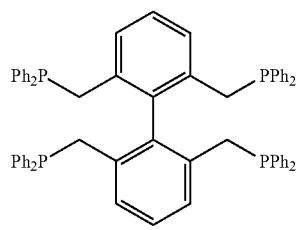

Comparative Ligand B

Comparative Ligand B is BISBI (neither a monophosphine nor a tetradentate phosphine) which is known to produce an active and selective hydroformylation catalyst. Methods of preparation for BISBI and examples of its use as a hydroformylation ligand may be found for example in U.S. Pat. No. 4,694,109. The BISBI used in the Comparative Experiments below was purchased from Proactive Molecular Research of Alachua, Fla. and used as received. The structure of BISBI (Ligand B) is shown in FIG. 2.

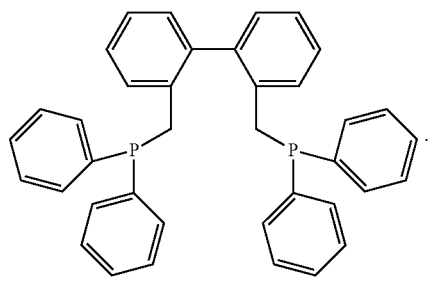

FIG 2

Comparative Ligand B; BISBI.

General Procedure

Unless otherwise indicated, examples and comparative experiments are conducted in 90 mL flow-through Fisher Porter reactors equipped with means for accurate control of temperatures and gas flows. Reactor off gases are analyzed by online GC to determine partial pressures. Mixing in the flow-through reactor is effected by continuous gas flow via a sparger at the bottom of the reactor. This reactor design is described in detail in U.S. Pat. No. 5,731,472, the teachings of which are incorporated by reference.

Reaction rates are expressed as moles of aldehyde produced per volume of catalyst solution per unit time (moles/L-hour); this value is additionally divided by the propylene partial pressure to help dampen the effects of small, unavoidable fluctuations in the propylene feed rate (rate/olefin). Product selectivity is expressed as the ratio of linear (normal) aldehyde versus branched (iso) aldehyde (N:I).

These Examples use an accelerated testing procedure, referred to herein as the block-in procedure to demonstrate the impact of the separation zone on the catalyst. Said testing procedure involves subjecting solubilized activated rhodium complex catalysts to low partial pressures and high temperatures for a much longer period of time than would be experienced during a normal continuous liquid recycle hydroformylation process in order to obtain meaningful results in a practical fashion. For instance, the catalytic deactivation and/or ligand usage as discussed herein that may occur during a continuous liquid recycle hydroformylation may take weeks to define quantitatively under normal aldehyde distillative recovery procedures because the catalyst is subjected to such vaporizer conditions for only a matter of minutes each day, whereas the accelerated test (block-in procedure) can be completed within hours or days by continuously maintaining the reaction product fluid at high aldehyde recovery type distillation temperatures for a prolonged period of time. Block-in segments comprise periods of time wherein the reactor is sealed under reduced pressure and high temperatures. This procedure is intended to simulate the effect of the separation zone on the catalyst solution.

Comparative Experiment A

A reactor is charged with tetraglyme (20 mL), rhodium (200 ppm), and Ligand A (1.5 equivalents). Hydroformylation is established under 20 psi CO, 50 psi $H_2$ and 20 psi propylene at 90° C., and baseline hydroformylation rates and N:I measured. After running overnight the reactor is sampled for HPLC to determine the concentration of free Ligand A, the reactor is vented down to a total pressure of 10 psi and blocked in at 115° C. overnight. Following the block in segment, hydroformylation is reinitiated at the original conditions and the catalyst solution sampled for HPLC; the block in procedure is then repeated for a second time.

Comparative Experiment B

The procedure of Comparative Experiment A is repeated, with the exception of the amount of Ligand A added (5 equivalents).

Examples 1-4

The procedures of Comparative Experiment A and B are repeated, with the exception of the addition of TPP (5 or 10 wt. %).

Result for Comparative Experiment A and B and Examples 8-11 are shown in Tables 1 and 2.

TABLE 1

| | TPP | Ligand A | Initial | | post 1st block in | | post 2nd block in | |
|---|---|---|---|---|---|---|---|---|
| | wt % | Equiv. | rate | N:I | rate | N:I | rate | N:I |
| C. E. A | 0 | 1.5 | 0.1254 | 42.7 | 0.0164 | 23.0 | 0.0119 | 18.0 |
| C. E. B | 0 | 5.0 | 0.1303 | 40.2 | 0.0337 | 27.7 | 0.0245 | 25.9 |
| Ex. 1 | 5 | 1.5 | 0.0308 | 19.3 | 0.0256 | 17.4 | 0.0240 | 16.4 |
| Ex. 2 | 5 | 5.0 | 0.0278 | 27.7 | 0.0274 | 26.9 | 0.0280 | 26.2 |
| Ex. 3 | 10 | 1.5 | 0.0215 | 14.3 | 0.0198 | 13.0 | 0.0187 | 13.2 |
| Ex. 4 | 10 | 5.0 | 0.0167 | 23.2 | 0.0165 | 23.7 | 0.0169 | 22.2 |

TABLE 2

| | Ligand A wt % by HPLC | | |
|---|---|---|---|
| | initial | After 1st block in | After 2nd block in |
| C. E. A | 0.0644 | 0.0087 | BDL |
| C. E. B | 0.4675 | 0.3438 | 0.3204 |
| Ex. 1 | 0.1135 | 0.0969 | 0.0836 |
| Ex. 2 | 0.5353 | 0.5372 | 0.5118 |
| Ex. 3 | 0.1244 | 0.1239 | 0.1072 |
| Ex. 4 | 0.5243 | 0.5399 | 0.5162 |

Both the hydroformylation rate and N:I demonstrated by catalyst solutions comprised solely of rhodium and Ligand A (Comparative Experiments A and B) drop significantly following the block in procedures as does the concentration of free Ligand A, which indicates ligand degradation. Although the initial hydroformylation rates are lower in Examples 1-4, the catalyst solutions of the invention demonstrate the ability to withstand the block in conditions, both in terms of a lessened degree of catalyst deactivation and a lower rate of ligand usage. Because chelating ligands are typically expensive, lowering consumption of tetradentate phosphine would improve process economics.

Comparative Experiments C-D

The procedure of Comparative Experiments A and B are repeated, with the exception of the use of Comparative Ligand B.

Comparative Experiments E-H

The procedure of Examples 1-4 are repeated, with the exception of the use of Comparative Ligand B.

Results for Comparative Experiments C-H are summarized in Table 3.

TABLE 3

| | TPP wt % | Com. Ligand B (equiv) | Initial | | post 1st block in | | post 2nd block in | |
|---|---|---|---|---|---|---|---|---|
| | | | rate | N:I | rate | N:I | rate | N:I |
| C.E. C | 0 | 1.5 | 0.0667 | 27.5 | 0.0143 | 1.8 | 0.0010 | 2.0 |
| C.E. D | 0 | 5.0 | 0.0640 | 35.8 | 0.0162 | 15.3 | 0.0127 | 18.2 |
| C.E. E | 5 | 1.5 | 0.0333 | 6.6 | 0.0261 | 5.9 | 0.0271 | 5.5 |
| C.E. F | 5 | 5.0 | 0.0218 | 10.7 | 0.0204 | 10.6 | 0.0192 | 10.0 |
| C.E. G | 10 | 1.5 | 0.0260 | 7.3 | 0.0229 | 7.0 | 0.0215 | 7.0 |
| C.E. H | 10 | 5.0 | 0.0175 | 8.9 | 0.0165 | 9.4 | 0.0161 | 9.0 |

It is noted that the catalysts comprised solely of rhodium and Comparative Ligand B are negatively impacted by the block in period, both in terms of catalyst deactivation and N:I. While the catalysts comprised of rhodium, TPP and Comparative Ligand B also show improved stability, they do not demonstrate an N:I in excess of 11. Without being bound by theory, this low N:I suggests that the rhodium-BISBI catalyst is more readily inhibited by TPP, and thus the resulting mixture of active complexes contains a relatively low amount of the active and selective rhodium-BISBI complex.

Examples 5-10

Each of six reactors is charged with tetraglyme (20 mL), rhodium (200 ppm), Ligand A (1.5 or 3 equivalents) and TPP (3-5 wt. %). Hydroformylation is established under 20 psi CO, 50 psi $H_2$ and 20 psi propylene at 90° C., and baseline hydroformylation rates and N:I measured. The reactors are blocked in twice at 10 psi and 115° C. overnight; after each block in segment the catalyst performance is determined under the original, pre-block in conditions. Next, additional Ligand A (one equivalent) is added to each reactor and the resulting change in performance measured. A summary of results appears in Table 4.

TABLE 4

| | TPP wt % | Ligand A eq | Initial rate | Initial N:I | post 1st block in rate | post 1st block in N:I | post 2nd block in rate | post 2nd block in N:I | Following additional Ligand A rate | Following additional Ligand A N:I |
|---|---|---|---|---|---|---|---|---|---|---|
| Ex. 5 | 3 | 1.5 | 0.0385 | 23.6 | 0.0278 | 18.7 | 0.0250 | 17.2 | 0.0282 | 24.0 |
| Ex. 6 | 3 | 3.0 | 0.0390 | 29.0 | 0.0330 | 26.6 | 0.0290 | 25.8 | 0.0312 | 28.0 |
| Ex. 7 | 4 | 1.5 | 0.0315 | 21.4 | 0.0275 | 18.7 | 0.0260 | 17.8 | 0.0276 | 24.0 |
| Ex. 8 | 4 | 3.0 | 0.0305 | 26.6 | 0.0293 | 25.8 | 0.0281 | 25.1 | 0.0288 | 27.2 |
| Ex. 9 | 5 | 1.5 | 0.0278 | 18.5 | 0.0257 | 17.0 | 0.0250 | 16.3 | 0.0242 | 21.5 |
| Ex. 10 | 5 | 3.0 | 0.0258 | 24.4 | 0.0275 | 23.0 | 0.0234 | 22.6 | 0.0236 | 24.3 |

It is noted that the initial hydroformylation rate is inversely proportional to TPP concentration, and that the N:I is directly proportional to Ligand A concentration; moreover the ability to increase N:I by the addition of more Ligand A near the end of the experiment is demonstrated. Without being bound by theory, this suggests that the observed catalysis is the result of a mixture of active rhodium complexes, and that furthermore, some amount of rhodium exists in a relatively inactive form, likely a rhodium-triphosphorous complex comprised of both Ligand A and TPP. The addition of more Ligand A restores the N:I back to the original value (prior to the block in periods) demonstrating that the system can recover after initial Ligand A degradation.

Comparative Experiment I

A reactor is charged with tetraglyme (20 mL), rhodium (350 ppm) and Ligand A (4 equivalents) at 90° C. The reactor is sparged briefly with 1:1 syn gas, and then sampled for HPLC to determine the concentration of free Ligand A. Air is then bubbled into the solution via syringe (250 mL) and the catalyst solution is sampled again for HPLC to determine the change in Ligand A concentration.

Example 11

The procedure of Comparative Experiment I is repeated with the exception of the addition of TPP (12 wt. %).
The results of Comparative Experiment I and Example 11 are summarized in Table 5.

TABLE 5

| | TPP (wt %) | Ligand A (wt %)— initial | Ligand A (wt %)— after air added | Ligand A Lost (%)— after air added |
|---|---|---|---|---|
| C. E. I | 0 | 0.7492 | 0.5439 | 27 |
| Ex. 11 | 12 | 0.8181 | 0.8030 | 1.8 |

The results of Table 5 show that the presence of TPP helps protect the tetraphosphine from degradation via oxidation that may occur during continuous operation due to small leaks in the system, or to the accidental introduction of air during equipment maintenance, etc.

What is claimed is:

1. A method for slowing deactivation of a catalyst and/or slowing tetraphosphine ligand usage in a hydroformylation process, the method comprising:
   (a) contacting an olefin with carbon monoxide, hydrogen and a catalyst, the catalyst comprising (A) a transition metal, (B) a tetraphosphine having the following structure:

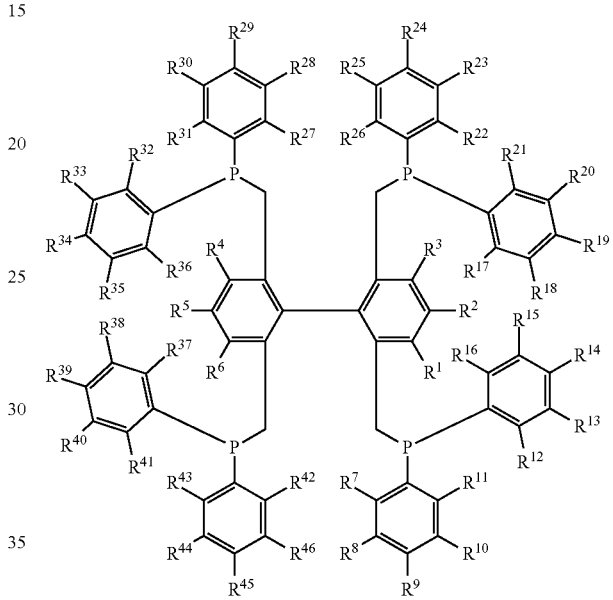

wherein each P is a phosphorous atom, and each of $R^1$-$R^{46}$ are independently hydrogen, a C1 to C8 alkyl group, an aryl group, an alkaryl group, or a halogen, and, optionally, (C) a monophosphine having the following structure:

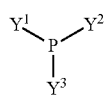

wherein P is a phosphorous atom, and each of $Y^1$-$Y^3$ are independently an aryl group, an alkaryl group, a cycloalkyl group, a benzyl group, a C3 to C8 alkyl group, an alkoxyl group of 1-8 carbons, an aryloxy group, or a halogen, the contacting conducted in one or more reaction zones and at hydroformylation conditions; and
   (b) adding additional monophosphine having the above structure to a reaction zone.

2. The method of claim 1, wherein the monophosphine is triphenylphosphine.

3. The method of claim 1, wherein the monophosphine is a bulky monophosphine.

4. The method of claim 1, wherein the transition metal comprises rhodium.

5. The method of claim 1, wherein each $R^1$-$R^{46}$ are hydrogen.

6. The method of claim 1, wherein the olefin is propylene.

7. The method of claim 1, wherein the decline in hydroformylation rate over time is less than in a process under identical conditions, with the exception of the absence of monophosphine.

8. The method of claim 1, wherein the rate of tetraphosphine ligand usage in the hydroformylation process is less than in a hydroformylation process under identical conditions, with the exception of the absence of monophosphine.

9. The method of claim 1, wherein the amount of monophosphine added is at least 40 moles of phosphine per mole of transition metal.

10. The method of claim 1, wherein the amount of monophosphine added to the reactor zone is greater than 1.5 weight percent of the reaction fluid in the reaction zone based on the total weight of the reaction fluid in the reaction zone.

\* \* \* \* \*